(12) United States Patent
Hattinger et al.

(10) Patent No.: US 11,718,128 B2
(45) Date of Patent: Aug. 8, 2023

(54) ERGONOMIC CENTRAL WHEEL LOCK FOR ULTRASOUND CONSOLES

(71) Applicant: GE Precision Healthcare LLC, Wauwatosa, WI (US)

(72) Inventors: Gerhard Hattinger, Pramet (AT); Christian Ruff, St. Johann im Pongau (AT)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 792 days.

(21) Appl. No.: 16/702,713

(22) Filed: Dec. 4, 2019

(65) Prior Publication Data
US 2021/0170791 A1 Jun. 10, 2021

(51) Int. Cl.
*B60B 33/02* (2006.01)
*A61B 8/00* (2006.01)
*F16D 65/28* (2006.01)

(52) U.S. Cl.
CPC .......... *B60B 33/021* (2013.01); *A61B 8/4427* (2013.01); *F16D 65/28* (2013.01); *A61B 8/4405* (2013.01); *A61B 8/4455* (2013.01); *B60B 2200/26* (2013.01)

(58) Field of Classification Search
CPC . B60B 33/021; B60B 2200/26; A61B 8/4427; A61B 2560/0425; A61B 2560/0437; F16D 65/28
See application file for complete search history.

(56) References Cited

U.S. PATENT DOCUMENTS

| | | | | |
|---|---|---|---|---|
| 4,309,791 A | * | 1/1982 | Aulik | B60B 33/021 16/35 R |
| 4,526,253 A | * | 7/1985 | Schmidt | B60B 33/0042 188/29 |
| 5,377,372 A | * | 1/1995 | Rudolf | B60B 33/021 16/35 R |
| 6,321,878 B1 | * | 11/2001 | Mobley | B60B 33/025 188/1.12 |
| 6,460,205 B1 | * | 10/2002 | Lewandowski | B60B 33/0092 5/625 |
| 6,575,052 B2 | * | 6/2003 | Toennesland | B60B 33/021 16/35 R |
| 6,843,349 B2 | * | 1/2005 | Walsh | B60B 33/0018 188/68 |
| 7,062,805 B2 | * | 6/2006 | Hopper | A61G 1/042 280/47.16 |
| 7,302,717 B2 | * | 12/2007 | Reinke | B60B 33/0068 5/600 |

(Continued)

*Primary Examiner* — Victor D Batson
*Assistant Examiner* — Matthew J Sullivan
(74) *Attorney, Agent, or Firm* — McAndrews, Held & Malloy, Ltd.; Jacob Groethe; David Bates (57) ABSTRACT

A system comprising a movable device including front wheels and rear wheels configured to swivel and roll, a braking system configured to lock the front wheels and the rear wheels to keep the front wheels and the rear wheels from rolling, a directionally locking system configured to keep the rear wheels from swiveling, first and second rear pedals configured to control the front and rear wheels to be in one of a locked state, a directionally locked state, or a released state, and first and second front pedals configured to control the front and rear wheels to be in one of a locked state or a released state.

20 Claims, 5 Drawing Sheets

(56) References Cited

U.S. PATENT DOCUMENTS

| | | | | |
|---|---|---|---|---|
| 7,810,822 B2* | 10/2010 | Figel | ................... | B60B 33/0039 |
| | | | | 188/29 |
| 7,922,183 B2* | 4/2011 | Figel | ................... | A61G 1/0287 |
| | | | | 280/47.38 |
| 7,926,145 B2* | 4/2011 | Liao | ................... | B60B 33/0073 |
| | | | | 188/19 |
| 8,024,101 B2* | 9/2011 | Froli | ................... | B60B 33/0081 |
| | | | | 701/1 |
| 8,789,662 B2* | 7/2014 | Childs | ................... | B60B 33/021 |
| | | | | 16/35 R |
| 8,819,894 B2* | 9/2014 | Hamasaki | ............. | B60B 33/025 |
| | | | | 16/35 R |
| 9,061,547 B2* | 6/2015 | Shih | ................... | B60B 33/021 |
| 9,173,795 B2* | 11/2015 | Heidlage | ................... | A61G 7/05 |
| 9,592,172 B2* | 3/2017 | Ferreri | ................... | A61G 15/002 |
| 9,994,072 B2* | 6/2018 | Lyon | ................... | B60B 33/0092 |
| 10,988,158 B2* | 4/2021 | Basco De Rosa Payne | ................. | |
| | | | | B62B 3/00 |
| 11,229,565 B2* | 1/2022 | Ethen | ................... | A61G 7/012 |
| 2014/0142428 A1* | 5/2014 | Kim | ................... | B60B 33/021 |
| | | | | 600/437 |

* cited by examiner

ERGONOMIC CENTRAL WHEEL LOCK FOR ULTRASOUND CONSOLES

FIELD

Certain embodiments relate to moving an object. More specifically, certain embodiments relate to ergonomic central wheel lock system devices for transporting objects.

BACKGROUND

Medical imaging machines such as, for example, an ultrasound scanner, may be used for imaging at least a portion of a patient's body as part of diagnostic procedures. The imaging machine may need to be moved within a room, or from room to room. When the imaging machine is not being moved, it may need to be secured to be in one position near the patient being scanned.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

An ergonomic central wheel lock system for devices for transporting objects, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

Referring to FIG. 5A.

Referring to FIG. 5B.

DETAILED DESCRIPTION

Certain embodiments may be found in a method and system for facilitating movement of an object such as, for example, an imaging system, a cart, a bed, etc., within a room as well as from room to room. The wheels may be locked to keep the object in place. The controls are ergonomically designed for smooth operation without interfering with a person who is pushing the object.

The foregoing summary, as well as the following detailed description of certain embodiments will be better understood when read in conjunction with the appended drawings. The figures provided illustrate diagrams of the functional blocks of various embodiments, and the functional blocks are not necessarily indicative of the division between mechanical parts.

It should be understood that the various embodiments are not limited to the arrangements and instrumentality shown in the drawings, and that various embodiments may be combined. Other embodiments may be utilized and structural, logical and electrical changes may be made without departing from the scope of the various embodiments. For example, sensors and/or motors, relays, circuitry including a display, etc., may be used to aid the mechanical parts. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also, as used herein, the term "imaging machine" broadly refers to an ultrasound scanner. However, other devices that need to be moved, which may include other types of portable imaging machines or parts of imaging machines, may also use an embodiment of the disclosure.

Figure 1A:
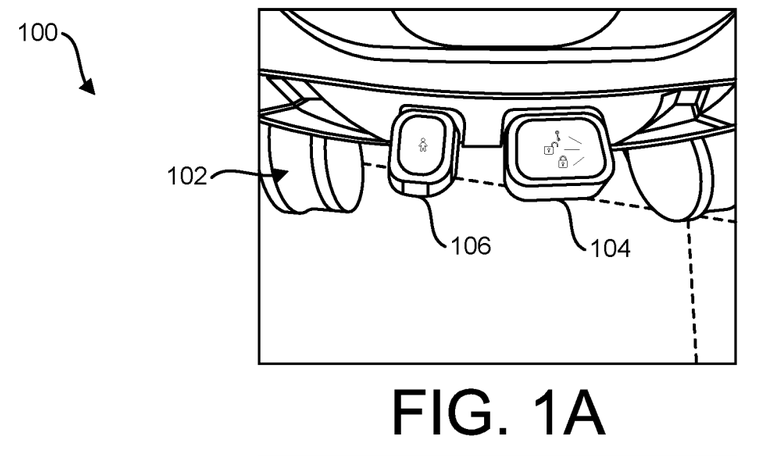
FIGS. 1A-1C illustrate example operation for a first pedal for an ergonomic central wheel lock system at a rear portion of an imaging system, in accordance with various embodiments.
Figure 1B:
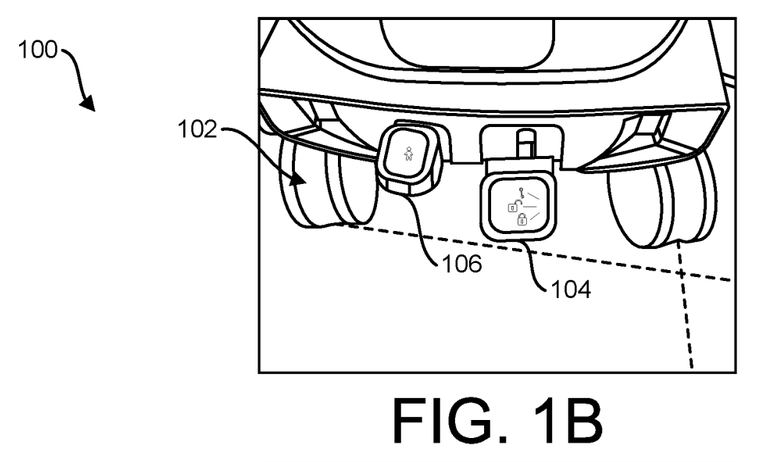
Figure 1C:
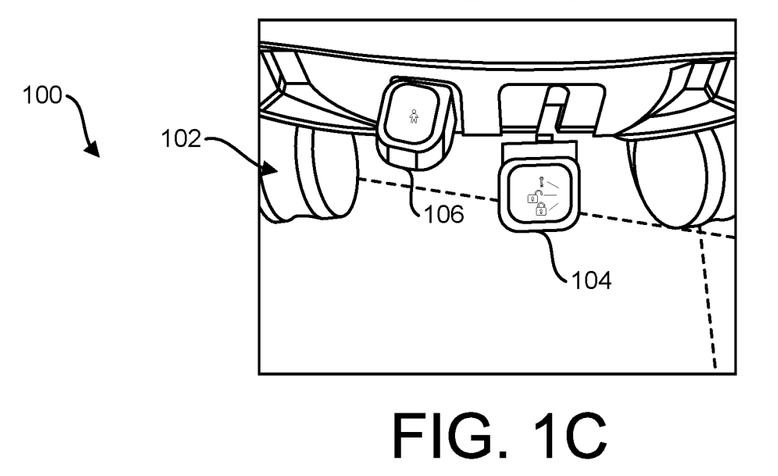
Figure 2A:
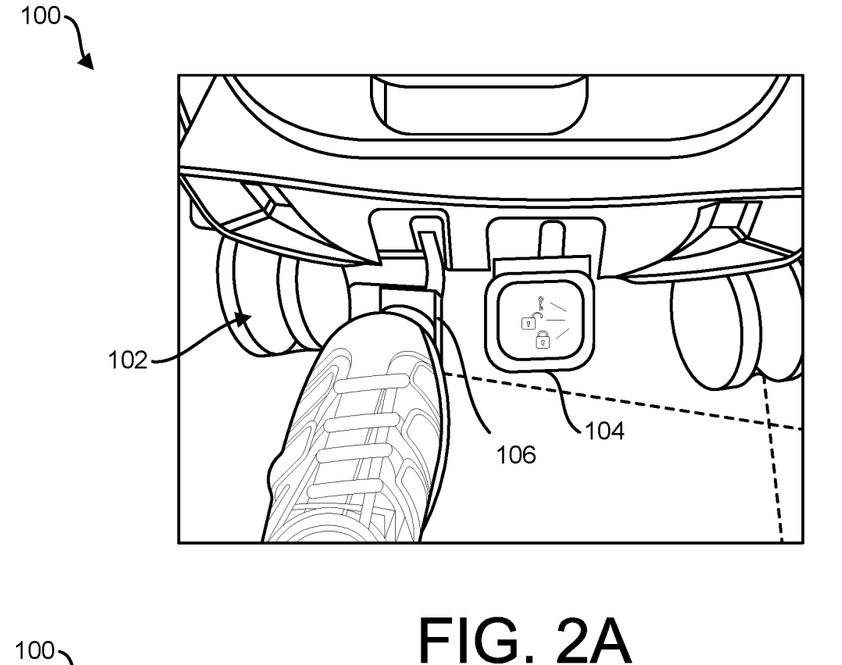
FIGS. 2A-2B illustrate example operation for a second pedal for the ergonomic central wheel lock system at the rear portion of an imaging system, in accordance with various embodiments.
Figure 2B:
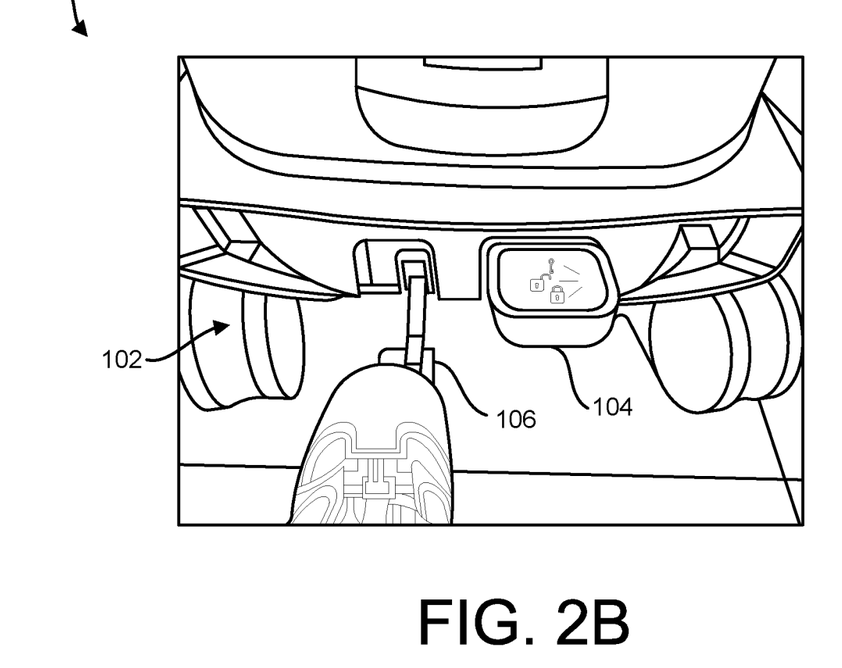
Figure 3A:
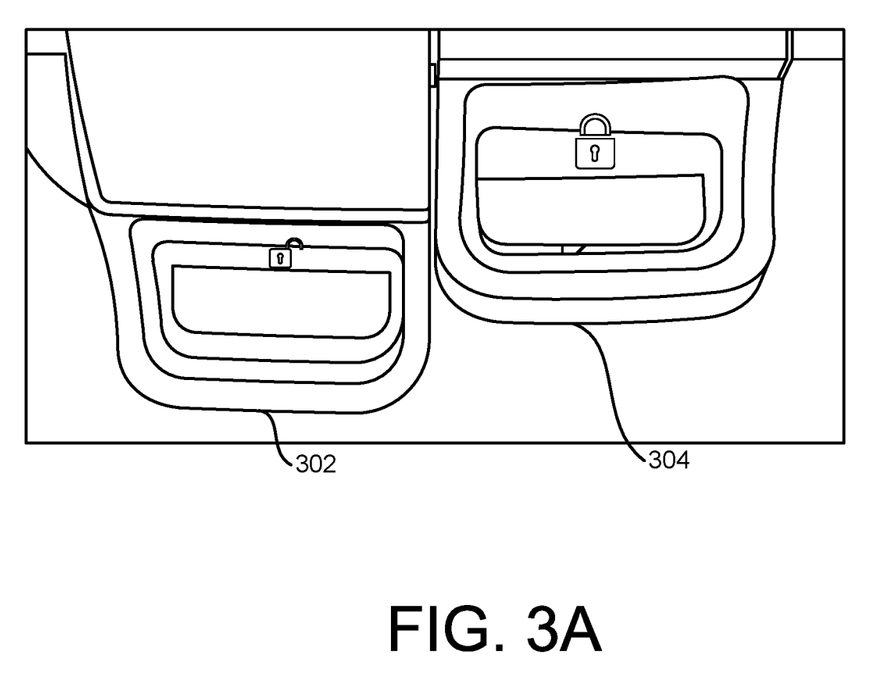
FIGS. 3A-3B illustrate an example ergonomic central wheel lock system for a front portion of an imaging system, in accordance with various embodiments.
Figure 3B:
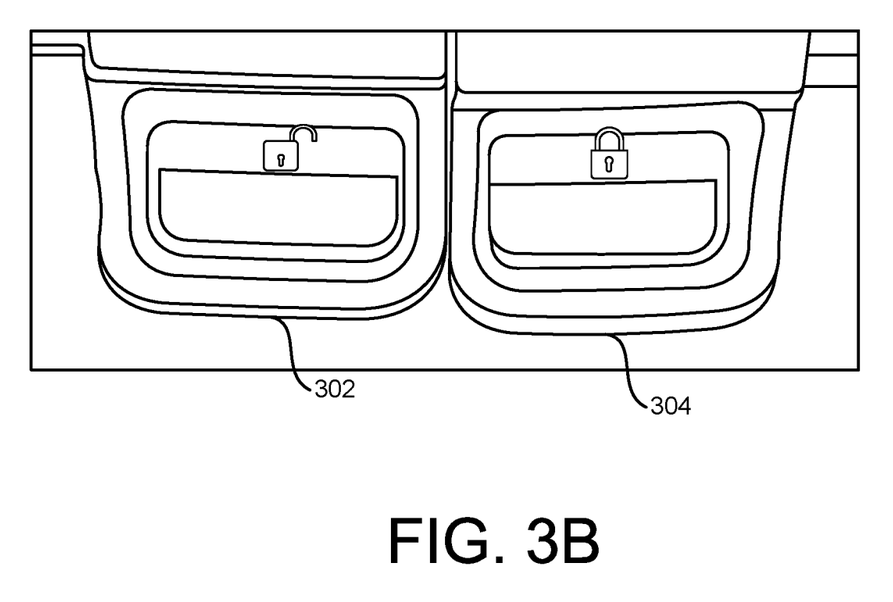

In an embodiment of the disclosure, FIGS. 1A-2B describe rear pedals 104 and 106 that control the three states (fully locked state, directionally locked state, and released state) of the wheels 102 of an imaging system 100, and FIGS. 3A-3B describe front pedals 302 and 304 that control two states (fully locked state and released state) of the three states of the wheels 102 of the imaging system 100. The rear pedals 104 and 106 work in concert with the front pedals 302 and 304 such that the front pedals 302 and 304 can enter either of its allowable states, and the rear pedals 104 and 106 will reflect the same state. Similarly, when the rear pedals 104 and 106 control the wheels 102 to the fully locked state or the released state, the front pedals 302 and 304 can be used to change to the other state.

Moreover, while the front pedals 302 and 304 cannot put the wheels 102 into the directionally locked state, the front pedals 302 and 304 can be used to change the directionally locked state to either the fully locked state or the released state regardless of which of the three states the wheels 102 may be in presently.

Various embodiments of the disclosure may have the front pedals 302 and 304 be able to control the wheels 102 to enter all three states using similar pedal system as shown in FIGS. 1A-1C.

When in the fully locked state, all of the wheels are locked in place so that they cannot roll in any direction. This state may be used, for example, when the imaging system 100 is in place by a patient or when the imaging system 100 is being stored.

When in the directionally locked state, the rear two wheels of the wheels 102 are directionally locked to roll only in forward and backward directions while the front two wheels of the wheels 102 are free to swivel and roll in any direction. This may be useful, for example, when the imaging system 100 is being moved from one location to another location down a hallway. Since the rear wheels 102 can only roll forward or backward, this allows the imaging system 100 to be pushed in a relatively stable manner down a hallway.

When in the released state, all four wheels 102 are free to swivel and roll in any direction. Accordingly, while this may not be conducive to rolling the imaging system 100 straight for a lengthy distance, this state makes it easy, for example, to maneuver the imaging system 100 in a smaller area where the imaging system 100 may need to be moved around objects or between objects.

Referring to FIGS. 1A-1C, there is shown a rear view of the imaging system 100 such as, for example, an ultrasound console comprising four wheels 102, a first rear pedal 104, and a second rear pedal 106. The wheels 102 may comprise two front wheels 102 in the front of the imaging system 100 and two rear wheels 102 in the back of the imaging system 100. The wheels 102 may generally be in three states—the fully locked state, the directionally locked state, and the released state. The wheel states may be changed using the rear pedals 104 and 106. The rear pedals 104 and 106 may both have three positions—top, middle, and bottom.

As shown in FIG. 1A, when the first rear pedal 104 is in the top position, the wheels are in the directionally locked state. As shown in FIG. 1B, when the first rear pedal 104 is in the middle position, the wheels are in the released state. As shown in FIG. 1C, when the first rear pedal 104 is in the bottom position, the wheels are in the fully locked state. Accordingly, it can be seen that when the first rear pedal 104 is in the top position, and the second rear pedal 106 is in its normal top position, there is maximum clearance between the rear pedals 104 and 106 and the floor, thereby allowing a user to push the imaging with minimal interference from the rear pedals 104 and 106.

When the first rear pedal 104 is in the top position, pressing the first rear pedal 104 slightly puts it to the middle position of FIG. 1B. When the first rear pedal 104 is pressed further, it is put in the bottom position of FIG. 1C. Accordingly, the first rear pedal 104 can be put from the top position to the middle position, then from the middle position to the bottom position, or immediately from the top position to the bottom position.

The second rear pedal 106 may be spring loaded to be normally in the top position. When the second rear pedal 106 is pressed slightly to the middle position as illustrated in FIG. 2A, the first rear pedal 104 is moved from the bottom position to the middle position. When the first rear pedal 104 is in the top position or the middle position, there is no effect on the first rear pedal 104 when the second rear pedal 106 is pressed to the middle position.

When the second rear pedal 106 is pressed to the bottom position as illustrated in FIG. 2B, the first rear pedal 104 is moved to the top position. Accordingly, the first rear pedal may be moved from the bottom position to the middle position, then from the middle position to the top position, or directly from the bottom position to the top position. When the first rear pedal 104 is in the top position, moving the second rear pedal 106 to the middle position or the bottom position does not affect the first rear pedal 104.

When the second rear pedal 106 is released after pressing it either to the middle position or the bottom position, the second rear pedal 106 goes back to its normal top position. In some embodiments of the disclosure, the second rear pedal 106 may not be able to move when the first rear pedal 104 is in the top position.

Therefore, when a user is moving the imaging system 100 from one location to another location nearby, the wheels 102 may be transitioned from the fully locked state to the released state to maneuver the imaging system 100 to the desired location, and then the wheels 102 of the imaging system 100 may be placed in a fully locked state.

When moving the imaging system 100 from one location to a location further away, the wheels 102 may be transitioned from the fully locked state to the released state to maneuver the imaging system 100 out of a room, and then the wheels 102 of the imaging system 100 may be placed in a directionally locked state to make it easier to push the imaging system 100 down a hallway. When the desired room is reached, the wheels 102 may be transitioned, for example, from the directionally locked state to the released state sot that the imaging system 100 can be located as desired in the room. The wheels 102 may then be placed in the fully locked state to keep it in place.

FIGS. 3A-3B illustrate an example ergonomic central wheel lock system for a front portion of an imaging system, in accordance with various embodiments. Referring to FIGS. 3A and 3B, there are shown the first and second front pedals 302 and 304. When the imaging system is in the fully locked state, the first front pedal 302 and the second front pedal 304 may be in the top position.

To put the wheels 102 into the released state, the first front pedal 302 may be pressed down. The second front pedal 304 may be pressed down to put the wheels 102 in the fully locked state. Accordingly, the first front pedal 302 may return to the top position. In an embodiment of the disclosure, the first front pedal 302 may remain in the bottom position after being pressed, and the second front pedal 304 may return to the top position after it is released from being pressed down.

While FIGS. 1A-3B describe an imaging system 100 such as, for example, an ultrasound console, various embodiments of the disclosure may be used for any object that needs to be moved and then locked in place. Accordingly, the ergonomic central wheel lock described in FIGS. 1A-2B may be used for a cart, a bed, rolling tray, etc.

Figure 4:
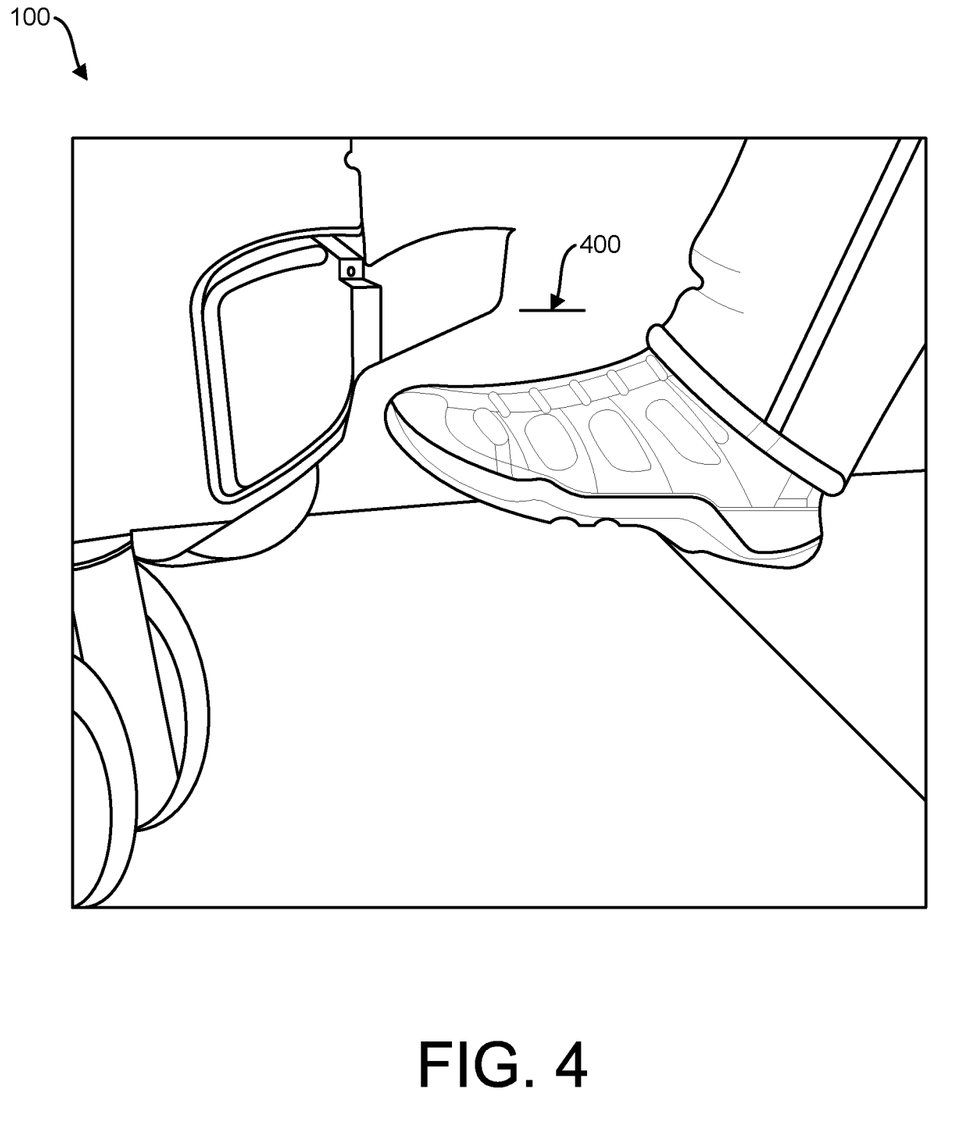
FIG. 4 is an illustration of an example ergonomic central wheel lock system for a rear portion of an imaging system when the imaging system is being moved, in accordance with various embodiments.

FIG. 4 is an illustration of an example ergonomic central wheel lock system for a rear portion of an imaging system when the imaging system is being moved, in accordance with various embodiments. Referring to FIG. 4, there is shown a rear view of the imaging system 100 where the wheels 102 are directionally locked. Accordingly, it can be seen that there is maximum clearance 400 from the rear pedals 104 and 106 in the top position to the floor. This may allow the person pushing the imaging system 100 additional room where his feet will not be entangled by the rear pedals 104 and 106.

Figure 5A:
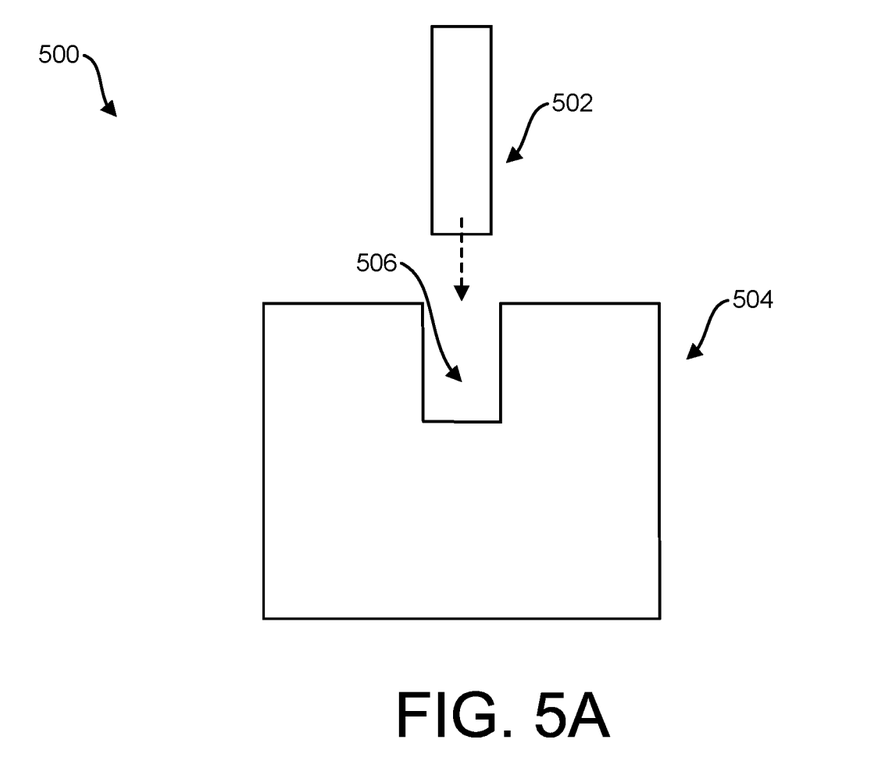
FIG. 5A is a side view of an example directionally locking mechanism, in accordance with various embodiments.

FIG. 5A is a side view of an example directionally locking mechanism, in accordance with various embodiments. Referring to FIG. 5A, there is shown the locking mechanism 500 comprising a locking bolt 502, a receiving bracket 504, and a bolt hole 506. The receiving bracket 504 may be, for example, coupled to a rear wheel 102. When the rear wheels 102 are put in the released state, the locking bolt 502 is not in the bolt hole 506, thus allowing the rear wheel 102 to roll in any direction. When the rear wheels 102 are put in the directionally locked state, the locking bolt 502 may be released. When the locking bolt 502 drops into the bolt hole 506, the rear wheel 102 may be restricted to rolling in specific directions such as, for example, forward/backward.

Figure 5B:
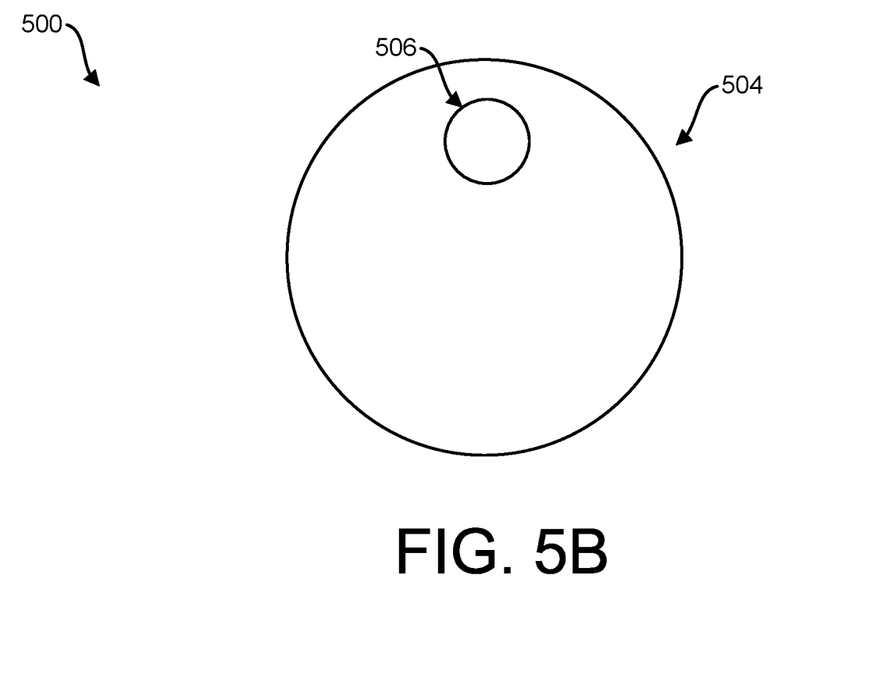
FIG. 5B is a top view of an example directionally locking mechanism, in accordance with various embodiments.

FIG. 5B is a top view of an example directionally locking mechanism, in accordance with various embodiments. Referring to FIG. 5B, there is shown the bolt hole 506 in the receiving bracket 506. As can be seen, when the locking bolt 502 is not aligned with the bolt hole 506, the rear wheel 102 may still roll in any direction. However, when the rear wheel 102 aligns during its rolling such that the locking bolt 502 can drop into the bolt hole 506, the rear wheel 102 can only roll in the desired direction such as, for example, forward/backward.

Although a specific mechanism was shown for the sake of illustration, various other mechanisms may be used for directionally locking the rear wheels 102. For example, rather than a round bolt hole 506, there may be a different shaped bolt hole 506. Also, rather than a bolt hole 506, there may be a slot 506 where the locking bolt 502 may be any shape that fits into the slot 506. Additionally, the bolt hole may 506 may be different shapes such as, for example, an inverted pyramid shape and the locking bolt 502 may also be an inverted pyramid shape to fit into the bolt hole 506.

Accordingly, the locking mechanism 500 may be any of various mechanisms known to those skilled in the art. For example, the mechanism 500 may also be an electrical brake system such as for example, an electro-magnet 502 that may be energized to be attracted to a metal plate 506 to keep the rear wheel 102 oriented in a desired direction.

Additionally, a braking mechanism for locking the wheels 102 in a fully locked state is well known to those skilled in the art, and thus will not be described in detail. For example, the braking mechanism may exert a mechanical force to keep the wheels 102 from rolling, or the braking mechanism may exert a magnetic force to keep the wheels 102 from rolling.

Furthermore, while an example was used for an imaging system 100 having four wheels 102, various embodiments of the disclosure may be applied to any mobile device with any number of wheels 102.

Various embodiments of the disclosure may also have the front pedals 302 and 304 provide the same functionality as the rear pedals 104 and 106.

Accordingly, it can be seen that the disclosure provides for a system comprising a movable device comprising front and rear wheels 102, where the front and the rear wheels 102 may be configured to swivel and roll, first and second rear pedals 104 and 106 may be configured to control the front and rear wheels 102 in one of a fully locked state, a directionally locked state, or a released state, and first and second front pedals 302 and 304 configured to control the front and rear wheels 102 in one of the fully locked state or the released state. The fully locked state may prevent the front wheels and the rear wheels 102 from rolling, the directionally locked state may keep the rear wheels 102 from swiveling, the released state may allow the front wheels and the rear wheels to roll and/or swivel.

The first and second rear pedals 104 and 106 and the first and second front pedals 302 and 304 may be operationally coupled to each other. Each of the first rear pedal 104 and the second rear pedal 106 may be configured to be in one of a top position, a middle position, or a bottom position.

When the first rear pedal 104 is in the top position, the rear wheels 102 may be in a directionally locked state. When the first rear pedal 104 is in the middle position, the front wheels and the rear wheels 102 may be in a released state where the front wheels and the rear wheels 102 may be free to swivel and/or roll. When the first rear pedal 104 is in the bottom position, the front wheels and the rear wheels 102 may be in a fully locked state where the front wheels and the rear wheels 104 are not able to roll.

When the first rear pedal 104 is in the bottom position, and the second rear pedal 106 is pressed to a middle position, the first rear pedal 104 may move to the middle position to put the front wheels and the rear wheels 102 in a released state. When the first rear pedal 104 is in the bottom position or the middle position, and the second rear pedal 106 is pressed to a bottom position, the first rear pedal 104 may move to the top position to put the rear wheels 102 in the directionally locked state. The second rear pedal 106 may be, for example, spring loaded to return to the top position upon release of the second rear pedal 106.

Furthermore, each of the first front pedal 302 and the second front pedal 304 may be configured to be in one of a top position or a bottom position. When the first front pedal 302 is in the top position, the front wheels and the rear wheels 102 may be in a fully locked state where the front wheels and the rear wheels 102 are not able to roll. When the first front pedal 302 is in the bottom position, the front wheels and the rear wheels 102 may be in a released state where the front wheels and the rear wheels 102 are free to swivel and/or roll. When the first front pedal 302 is in the bottom position, and the second front pedal 304 is pressed to a bottom position, the first front pedal 302 may move to the top position to put the rear wheels 102 in the fully locked state. The second front pedal 304 may be, for example, spring loaded to return to the top position upon release of the second front pedal 304.

The disclosure may also provide for an imaging system 100 comprising front wheels and rear wheels 102 configured to swivel and roll, first and second rear pedals 104 and 106 configured to control the front and rear wheels 102 in one of a fully locked state, a directionally locked state, or a released state, and first and second front pedals 302 and 304 configured to control the front and rear wheels 102 in one of a fully locked state or a released state. The first and second rear pedals 104 and 106 may be operationally coupled to the first and second front pedals 302 and 304, where the fully locked state may prevent the front wheels and the rear wheels 102 from rolling, the directionally locked state may keep the rear wheels 102 from swiveling, and the released state may allow the front wheels and the rear wheels 102 to roll and/or swivel.

Each of the first rear pedal 104 and the second rear pedal 106 may be configured to be in one of a top position, a middle position, or a bottom position. When the first rear pedal 104 is in the top position, the rear wheels 102 may be in a directionally locked state. When the first rear pedal 104 is in the middle position, the front wheels and the rear wheels 102 may be in a released state. When the first rear pedal 104 is in the bottom position, the front wheels and the rear wheels 102 may be in a fully locked state.

When the first rear pedal 104 is in the bottom position, and the second rear pedal 106 is pressed to a middle position, the first rear pedal 104 may move to the middle position to put the front wheels and the rear wheels 102 in a released state. When the first rear pedal 104 is in the bottom position or the middle position, and the second rear pedal 106 is pressed to a bottom position, the first rear pedal 104 may move to the top position to put the rear wheels 102 in the directionally locked state.

Each of the first front pedal 302 and the second front pedal 304 may be configured to be in one of a top position or a bottom position, where, when the first front pedal 302 is in the top position, the front wheels and the rear wheels 102 may be in a fully locked state where the front wheels and the rear wheels 102 are not able to roll. When the first front pedal 302 is in the bottom position, the front wheels and the rear wheels 102 may be in a released state where the front wheels and the rear wheels 102 are free to swivel and/or roll. When the first front pedal 302 is in the bottom position, and the second front pedal 304 is pressed to a bottom position, the first front pedal 302 may move to the top position to put the rear wheels 102 in the fully locked state.

As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y,z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations.

Accordingly, the present disclosure may be realized with mechanical and/or electrical devices. While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. A system, comprising:
    a movable device comprising front wheels and rear wheels, wherein the front wheels and the rear wheels are configured to swivel and roll;
    first and second rear pedals configured to control the front and rear wheels in any of a fully locked state, a directionally locked state, or a released state; and
    first and second front pedals configured to control the front and rear wheels in either of the fully locked state or the released state, but not the directionally locked state,
    wherein the fully locked state prevents the front wheels and the rear wheels from rolling,
    the directionally locked state allows the front wheels to swivel but keeps the rear wheels from swiveling, and
    the released state allows the front wheels and the rear wheels to roll and swivel.

2. The system of claim 1, wherein the first and second rear pedals and the first and second front pedals are operationally coupled to each other.

3. The system of claim 1, wherein each of the first rear pedal and the second rear pedal is configured to be in one of a top position, a middle position, or a bottom position.

4. The system of claim 3, wherein when the first rear pedal is in the top position, the rear wheels are in a directionally locked state.

5. The system of claim 3, wherein when the first rear pedal is in the middle position, the front wheels and the rear wheels are in a released state wherein the front wheels and the rear wheels are free to perform one or both of swiveling and rolling.

6. The system of claim 3, wherein when the first rear pedal is in the bottom position, the front wheels and the rear wheels are in a fully locked state wherein the front wheels and the rear wheels are not able to roll.

7. The system of claim 3, wherein when the first rear pedal is in the bottom position, and the second rear pedal is pressed to a middle position, the first rear pedal is moved to the middle position to put the front wheels and the rear wheels in a released state.

8. The system of claim 3, wherein when the first rear pedal is in the bottom position or the middle position, and the second rear pedal is pressed to a bottom position, the first rear pedal is moved to the top position to put the rear wheels in the directionally locked state.

9. The system of claim 3, wherein the second rear pedal is spring loaded to return to the top position upon release of the second rear pedal.

10. The system of claim 1, wherein each of the first front pedal and the second front pedal is configured to be in one of a top position or a bottom position.

11. The system of claim 10, wherein when the first front pedal is in the top position, the front wheels and the rear wheels are in a fully locked state wherein the front wheels and the rear wheels are not able to roll.

12. The system of claim 3, wherein when the first front pedal is in the bottom position, the front wheels and the rear wheels are in a released state wherein the front wheels and the rear wheels are free to perform one or both of swivel and roll.

13. The system of claim 3, wherein when the first front pedal is in the bottom position, and the second front pedal is pressed to a bottom position, the first front pedal is moved to the top position to put the rear wheels in the fully locked state.

14. The system of claim 10, wherein the second front pedal is spring loaded to return to the top position upon release of the second front pedal.

15. An imaging system, comprising:
    front wheels and rear wheels configured to swivel and roll;
    first and second rear pedals configured to control the front and rear wheels in any of a fully locked state, a directionally locked state, or a released state; and
    first and second front pedals configured to control the front and rear wheels in either of the fully locked state or the released state, but not the directionally locked state,
    wherein the first and second rear pedals are operationally coupled to the first and second front pedals,
    the fully locked state prevents the front wheels and the rear wheels from rolling,
    the directionally locked state allows the front wheels to swivel but keeps the rear wheels from swiveling, and
    the released state allows the front wheels and the rear wheels to roll and swivel.

16. The system of claim 15, wherein each of the first rear pedal and the second rear pedal is configured to be in one of a top position, a middle position, or a bottom position, wherein:
    when the first rear pedal is in the top position, the rear wheels are in a directionally locked state,
    when the first rear pedal is in the middle position, the front wheels and the rear wheels are in a released state wherein the front wheels and the rear wheels are free to perform one or both of swiveling and rolling, and
    when the first rear pedal is in the bottom position, the front wheels and the rear wheels are in a fully locked state.

17. The system of claim 16, wherein when the first rear pedal is in the bottom position, and the second rear pedal is pressed to a middle position, the first rear pedal is moved to the middle position to put the front wheels and the rear wheels in a released state.

18. The system of claim 16, wherein when the first rear pedal is in the bottom position or the middle position, and the second rear pedal is pressed to a bottom position, the first rear pedal is moved to the top position to put the rear wheels in the directionally locked state.

19. The system of claim 15, wherein each of the first front pedal and the second front pedal is configured to be in one of a top position or a bottom position, wherein:
  when the first front pedal is in the top position, the front wheels and the rear wheels are in a fully locked state wherein the front wheels and the rear wheels are not able to roll, and
  when the first front pedal is in the bottom position, the front wheels and the rear wheels are in a released state wherein the front wheels and the rear wheels are free to perform one or both of swivel and roll.

20. The system of claim 19, wherein when the first front pedal is in the bottom position, and the second front pedal is pressed to a bottom position, the first front pedal is moved to the top position to put the rear wheels in the fully locked state.

* * * * *